United States Patent [19]

Kahle, II et al.

[11] Patent Number: 5,600,035
[45] Date of Patent: Feb. 4, 1997

[54] POSITIVE PHOTOACTIVE COMPOUNDS BASED ON 2,6-DINITRO BENZYL GROUPS AND 2,5-DINITRO BENZYL GROUPS

[75] Inventors: Charles F. Kahle, II, McCandless Twp., Allegheny County; Neil D. McMurdie, Ross Twp., Allegheny County; Raphael O. Kollah, Shaler Twp., Allegheny County; Daniel E. Rardon, Pittsburgh; Gregory J. McCollum, Hampton Twp., Allegheny County, all of Pa.

[73] Assignee: PPG Industries, Inc., Pittsburgh, Pa.

[21] Appl. No.: 274,614

[22] Filed: Jul. 13, 1994

[51] Int. Cl.$^6$ .................................................. C07C 205/00
[52] U.S. Cl. ........................... 568/932; 568/933; 568/705; 568/662; 568/626; 568/67; 568/66; 568/57; 568/56; 568/44; 568/39; 564/336; 564/284; 564/282; 560/254; 560/163; 560/32; 558/268; 558/265; 558/59; 549/551
[58] Field of Search ................................ 568/932, 39, 44, 568/56, 57, 66, 67, 626, 662, 705, 933; 560/32, 163, 254; 558/268, 265, 59; 549/551; 564/336, 284, 282

[56] References Cited

U.S. PATENT DOCUMENTS

| | | | |
|---|---|---|---|
| 3,325,568 | 6/1967 | Richter | 260/930 |
| 4,203,928 | 5/1980 | Meyer. | |
| 4,551,416 | 11/1985 | Chandross et al. | 430/311 |
| 4,632,900 | 12/1986 | Demmer et al. | 430/323 |
| 4,666,820 | 5/1987 | Chandross et al. | 430/270 |
| 4,910,345 | 3/1990 | Streicher et al. | |
| 4,975,351 | 12/1990 | Akaki et al. | 430/190 |
| 5,082,976 | 1/1992 | Blank et al. | 568/431 |
| 5,134,054 | 7/1992 | Iwasaka et al. | 430/192 |
| 5,166,036 | 11/1992 | Seio et al. | 430/313 |
| 5,230,984 | 5/1993 | Tachiki et al. | 430/270 |

FOREIGN PATENT DOCUMENTS

| | | |
|---|---|---|
| 63-247749 | 10/1987 | Japan. |
| 63-146029 | 6/1988 | Japan. |
| 03-141357 | 6/1991 | Japan. |
| 03-131626 | 6/1991 | Japan. |
| 150832 | 1/1992 | U.S.S.R.. |

OTHER PUBLICATIONS

CA 88:21572 (1977).
CA 82:138696 (1974).
Abstract: Letrahedron Letters No. 49–50, pp. 4397–4400, 1974. Pergamon Press Orientierungseffekte auf Charge–Transfer–Wechselwirkungen, IV$^1$) Die Beiden Diastereomeren 4,7–Dimethoxy–12, 15–dinitro [2.2] paracyclophane in Great Britain., Heinz A. Staab & Heinz Haffer, Printed in Great Britain.
Abstract: Chem. Ber. 110, 3358–3365 (1977) Orientierungseffekte auf Charge–Transfer–Wechselwirkungen, VIII$^1$) Diastereomere 4,7–Dimethoxy–12, 15–dinitro [2.2] paracyclophane Heinz A. Staab and Heinz Haffer.
Stabb, H. A. et al., "The Effects of Orientation on Charge–Transfer Interactions, IV, The Two Diastereomers, 4,7–Dimethoxy–12, 15–Dinitro [2.2] Paracyclophanes". (Tetrahedron Letters, No. 49–50, 4397–4400 (1974)).
Stabb, H. A. et al., "Orientation Effects on Change–Transfer Interactions, VIII, Diastereo 4,7–Dimethoxy–12, 15–Dinitro [2.2] Paracyclophanes"., (Chem. Ber. 110, 3359–3365 (1977).
Houlihan, F. M., et al., "Synthesis of 4–(t–butoxycarbonyl)–2,6–dinitrobenzyl Tosylate, a Potential One Component Photoacid Generator and Dissolution Inhibitor Solubilizable Through Chemical Amplification, " Proceedings of the ACS Division of PMSE, Spring Meeting, 1992, San Francisco, CA, vol. 66, pp. 38–39.
*Chem. Abstracts*, 71:40389f, Polycondensation of compounds having methyl or active methylene groups with organic dihalogen compounds (1969).
*Chem. Abstracts*, 51:2858e, m–Nitrobenzyl chlorides. (1957).
Cameron, J. F. et al., J.Am. Chem Soc., 113, 4303–4313 (1991) Photogeneration of Organic Bases from o–Nitrobenzyl–Derived Carbamates.

*Primary Examiner*—Paul J. Killos
*Attorney, Agent, or Firm*—Dennis G. Millman; Paul S. Chirgott

[57] ABSTRACT

Photoreactive compounds are synthesized from 2,5- or 2,6-dintrobenzyl groups. Also disclosed are methods of synthesizing reactive monomers containing 2,5- or 2,6-dintrobenzyl groups.

18 Claims, No Drawings

POSITIVE PHOTOACTIVE COMPOUNDS BASED ON 2,6-DINITRO BENZYL GROUPS AND 2,5-DINITRO BENZYL GROUPS

BACKGROUND OF THE INVENTION

The present invention relates to photoactive monomers, to oligomeric intermediates containing said monomers, to photoreactive polymers containing said monomers useful as positive acting photoresists, and to methods for making said monomers, intermediates, and polymers.

Photoreactive polymers are useful as binder resins in photoresist compositions employed in photodevelopment of electronic components such as circuit boards and other products. Circuit boards are manufactured in a number of processing steps which rely on the use of photoreactive coatings (or photoresists) that photochemically produce a difference in solubility between the photoexposed areas and the unexposed areas. In general, two classes of photoresist exist: positive acting resists and negative acting resists. A positive acting resist becomes more soluble in a developer solution when exposed to actinic radiation, and a negative acting resist becomes less soluble in a developer solution when exposed to actinic radiation. For many applications a positive acting resist is preferred. An object of the present invention is to provide novel positive acting photoresists.

One situation in which positive acting resists are preferred is in the case of circuit boards that have through holes that permit connection of one board to an adjacent board in a stack. These through holes are copper coated and must be protected from etchants. One method to accomplish this is the use of an applied, preformed film which covers the hole and protects the copper from etchants during processing. A more recent development is the electrodeposition of photoresist, and this approach has significant advantages over applied film for coating the copper in the holes with photoresist without plugging. An objective has been to create a positive acting, electrodepositable photoresist which could coat the hole, protecting it from etchants, and then be removed from the hole more easily than negative photoresists. Negative acting resists have disadvantages for protecting through holes because of the inherent difficulties associated with removing a crosslinked material from a small space such as a through hole. Furthermore, there is difficulty in exposing negative photoresist material that is located within a hole in order to crosslink such a resist so that it can protect the copper. With a positive photoresist, on the other hand, the holes need not be exposed since the resist material in the holes does not need to become crosslinked in order to serve its purpose.

Diazo functional moieties such as quinonediazidesulfone derivatives having structures (1) and (2) in which R is typically chlorine (e.g., sulfonyl chloride)

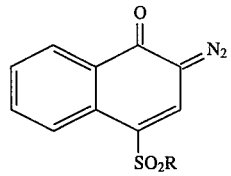 (1)

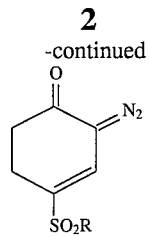 (2)

are well known as photoreactive groups for use in positive acting photoresists. In the synthesis of those prior art compounds, sulfonyl chloride is condensed with hydroxyl or amino functionalities attached to monomeric, oligomeric, or polymeric materials. The quinonediazidesulfone derivatives in such a photoresist function by photochemically generating an intermediate ketene which reacts with water to form a carboxylic acid. Photoexposed areas contain salt-forming carboxylic acid groups which dissolve in basic developing solutions. Dissolution of unexposed area in a basic developer is inhibited by the presence of the unreacted hydrophobic components (1) or (2). If water is not present the ketene will react with other hydroxyl groups to form undesirable esters which are not subject to solubilization by a developer. Since the photoreaction mechanism requires the presence of water to work well, a burden is imposed on the user to process the circuit boards under carefully controlled conditions so that the boards all undergo exactly the same dehydration bakes and are handled in very carefully controlled humidity conditions. It would be desirable to have available alternative chemistry for positive acting photoresists that would not entail such precautions.

Many of the prior art photosensitive groups for positive photoresists include molecular groups that are hydrolytically sensitive, which limits the versatility of these groups for use in electrodepositable formulations, whether cationic or anionic. As reported in U.S. Pat. Nos. 5,166,036; 4,975,351 and 5,134,054 the storage stability of electrodepositable photoresists based on diazo containing materials is poor and is attributed to hydrolyric instability of the sulfonyl linkage. Examples of other hydrolytically unstable groups include acetals, polyesters, t-butoxycarbonyl (t-BOC) protected carboxylates or phenols, and sulfonate esters. When a cationic or anionic dispersion is electrodeposited on a conductive substrate, a pH of 12 to 14 or 1 to 2, respectively, may be created at the interface of the coating and the substrate. A pH of 12 to 14 may be created in the case of a cationic coating. It is well known that diazo functionalities are sensitive to both high and low pH conditions and will react to form undesirable reaction products. The other chemistries such as t-BOC protected groups, acetals, and esters are also subject to hydrolysis under certain conditions of high and low pH, especially under aqueous conditions. Furthermore, stability of the chemistry under coating conditions and post-coating bake conditions is often given little or no consideration in the prior art. After a substrate has been electrocoated it is usually necessary to bake the coating for a sufficient time to allow for complete coalescence as well as evaporation of water and any volatile organic components. In the case of heat-sensitive diazo functional materials, even short bake times at high temperatures can decompose the diazo compounds. The use of long bake times at lower temperatures severely reduces the processing speed for a manufacturer.

The irradiation of photoresist, in the case of circuit board manufacture, often occurs through a glass or plastic cover sheet. Radiation passing through such a cover sheet to reach the photoresist is predominantly that having wavelengths greater than approximately 315 nanometers. The principal wavelength used for irradiation of photoresists is the 365 nanometer wavelength of a mercury vapor ultraviolet lamp.

Therefore, a useful photoresist for printed circuit board manufacture is preferably sensitive to radiation having wavelengths greater than 315 nanometers, particularly to radiation in the vicinity of 365 nanometers.

Some prior art approaches to electrodepositable, positive photoresist rely on photo-generated solubilizing groups which are pendant to the main polymer chain of the photoresist polymer. The theoretical maximum quantum efficiency (the number of reactions divided by the number of photons impinging on the photoresist) of such a system is one, i.e., each photon entering the photoresist would ideally result in formation of a solubilizing group. However, the quantum efficiency is usually much less than one. In order to overcome this limitation on quantum efficiency, systems have been developed which rely on photogenerated catalysts so that one photoreaction produces one catalyst which promotes many other reactions. U.S. Pat. No. 5,230,984 uses photogenerated acid catalysts generated by exposures of 800 millejoules per square centimeter, which is a relatively high exposure dosage. Higher photosensitivity permitting lower exposure dosages would be desirable. Also, these prior art systems require a bake following photoexposure, which undesirably increases processing time. The use of a catalyst can also hurt resolution by diffusion into the surrounding polymer and causing reactions outside of the desired regions. Known photo generated catalysts are based on sulfonate esters of 2,6-dinitro-p-xylene.

A wide variety of nitrobenzyl alcohol structures are theoretically encompassed by generic structures in Japanese Patent Applications 63-146029, 03-131626, 03-141357, and 63-247749. These applications disclose nitro-containing benzyl alcohol derivatives specifically for use in applications employing short wavelength ultraviolet radiation in the region of 248 nanometers. They fail to recognize the surprisingly high photosensitivity at longer wavelengths (particularly 365 nanometers) of certain dinitrobenzyl structures. Furthermore the above-numerated Japanese applications are non-enabling as to a synthesis for the particular dinitro structures of the present invention. The syntheses disclosed in the Japanese publications for other species would not be suitable for producing the dinitrobenzyl alcohols of the present invention at practical yield levels. Furthermore, these applications fail to instruct the use of polymers derived from this material in electrodepositable compositions. In fact, the types of polyesters disclosed would be expected to be hydrolytically unstable due to the presence of ester groups.

SUMMARY OF THE INVENTION

The present invention is an approach to positive acting photochemistry which yields a substantial improvement in quantum efficiency by the use of photoreactive compounds synthesized from monomers including:

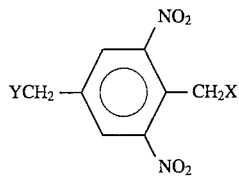

or

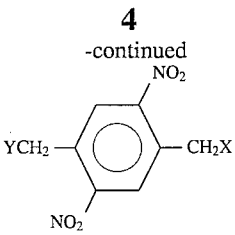

where X and Y may be the same or different member selected from the group consisting of: halogen, —OH, —OR, —O—SO$_3$R, —SR, and —NRR'. R and R' may be any of a wide variety of organic substituents, including substituted or unsubstituted alkyl, aryl, or aralkyl substitutents if further reaction is desired, the R or R' groups may include a reactive group such as a hydroxyl group. During photoreaction, the bond is broken between the carbon and the X in the CH$_2$X group.

The 2,6-dinitro structure (3) is preferred due to its high degree of photosensitivity. Thus, preferred embodiments of intermediates and polymers of the present invention may be derived from the monomer:

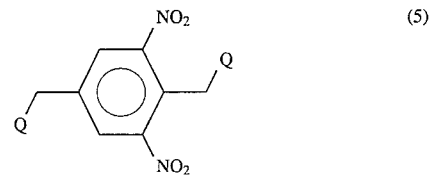

where Q is halogen or OH.

The dichloro species has been found to be particularly useful, and the diol species can be derived from the dichloro monomer. Both the chloride and hydroxyl groups are reactive with a wide variety of substances whereby intermediates and polymers can be synthesized from the dichloro and diol monomer (5). The oligomers or polymers thus formed are highly photoreactive and find use as positive acting photoresists and the like. These polymers and intermediates also form part of the present invention. The intermediates or polymers of the present invention include the photoreactive groups as defined above and at least one ether, ester, urethane, carbonate, thio, or amino group or combinations thereof. Each of these substitutents may include a reactive group (e.g., OH) to enable further reaction or copolymerization if desired.

Polymers can be prepared from monomers and intermediates having the defined dinitro benzyl structures which are hydrolytically and thermally stable to the processing conditions required for photoimaging, such as in the manufacture of circuit boards. Polymers such as polyurethanes, polysulfides, and polyethers can be produced and are known to be stable in electrocoating baths. Polyesters, polyamines, and polyquaternized amine polymers have also been prepared with the desirable dinitro groups of the present invention. Optionally, the photoreactive polymers may be combined with a polymer having salt forming groups to permit electrodepositing the photoresist composition onto conductive substrates.

Novel syntheses of the defined dinitro benzyl structures having high yields, as well as their use in making intermediates and polymers, are also part of the present invention. In particular, a novel process has been found for producing photoreactive dinitro dihalo benzyl compounds.

DETAILED DESCRIPTION

Although not wishing to be bound by a particular theory, it is believed that dinitro substitution in the benzyl group increases photosensitivity compared to mononitro substitution in prior art compounds. Even further enhancement of sensitivity is believed to be yielded by the 2,6-dinitro substitution. Not only does the structure of 2,6-dinitro or 2,5-dinitro substitution around a benzyl group provide good quantum efficiency, but it also provides the added benefit of chain scission of the backbone polymer to lower molecular weight fragments upon exposure to actinitic radiation. This enhances the solubility of exposed portions of the polymer during the developing process of a photoimaging process. The photochemistry relies on the photooxidation of the benzyl group by the nitro group. Each photoreaction causes at least two changes to a polymer containing the dinitro benzyl groups defined above—lower molecular weight and formation of a salt forming group-both of which enhance the sensitivity of the photoexposed material to developer. These changes work in concert to give excellent photosensitivities.

The dinitro photoreactive groups of the present invention are characterized by a benzene ring wherein at least one of the nitro groups is adjacent to a photo-scissionable group substituted on the ring. Photosensitivity of the scissionable group is enhanced by the adjacent nitro group (as in 2,5-dinitro substitution), and even greater photosensitivity is achieved in the case of two adjacent nitro groups (as in 2,6-dinitro substitution). The presence of one and preferably two nitro groups adjacent to the scissionable group also shifts peak sensitivity to longer wavelengths, e.g., toward the vicinity of 365 nanometers, which is a wavelength commonly used in commercial photoimaging processes.

In order to be incorporated into polymeric photoresists and the like, the photoreactive groups have a plurality of copolymerizable functional groups. A preferred functional group is a hydroxyl group, and preferred intermediates of the present invention therefore are diols. Although functionality greater than two is seldom needed, it should be understood that the present invention does not preclude functionality greater than two.

An important feature of the present invention is the discovery of a high yield synthesis of dinitro dihalo benzyl compounds, which themselves are novel, and which may be used directly to produce intermediates and polymers or to produce dinitro diol monomers which can then be used to produce other intermediates and polymers. The first step in the production of the novel monomers, intermediates, and polymers of the present invention is the synthesis of a dinitro bis(halomethyl) benzene monomer (described in Example 1), wherein commercially available α, α'-dichloro-p-xylene is nitrated to yield structure (6). The dihalo compound (6) may then be hydrolyzed to the dinitro diol intermediate of structure (7) as illustrated by Example 2.

EXAMPLE 1

SYNTHESIS OF 2,6-DINITRO 1,4-BIS(CHLOROMETHYL)BENZENE

Concentrated sulfuric acid (density 1.84, 95 milliliters), 13 milliliters of oleum (27–33%, density 1.94) and 150 milliliters of concentrated nitric acid (>90%, density 1.50) were combined in an ice bath cooled 1 liter flask equipped with mechanical stirring, condenser, and thermometer. The acid mixture exothermed slightly upon mixing. After the mixture cooled to below 25° C., α, α'-dichloro-p-xylene (35.0 grams, 0.2 mole) was added in small portions over 30 minutes so that the reaction temperature did not exceed 35° C. After addition of the dichloride was complete, a premixed acid solution prepared from 5.0 milliliter each of sulfuric and nitric acids and 2.0 milliliter of oleum was added to the reaction flask over 30 minutes. Stirring at room temperature was continued for an additional two hours to ensure complete reaction. The reaction mixture was added carefully to 1 kilogram of ice and allowed to cool. The precipitate was collected by filtration and washed with distilled water. The solid product was taken up in methylene chloride, washed 3 times with saturated sodium bicarbonate solution, and dried with magnesium sulfate. The solvent was evaporated, and the product was recrystallized from ethanol to give 37.6 grams (71%) of pure 2,6-dinitro-1,4-bis(chloromethyl)benzene (structure 6) with a melting point of 106° C. Also recovered from the reaction mixture were 10.5 grams of 2,5-dinitro-1,4-bis(chloromethyl)-benzene as a byproduct. The presence of both products was confirmed by NMR spectroscopy.

EXAMPLE 2

HYDROLYSIS OF 2,6-DINITRO-1,4-BIS(CHLOROMETHYL)BENZENE TO

THE CORRESPONDING DIOL

A mixture of 2,6-dinitro-1,4-bis(chloromethyl)benzene (structure 6)(1 grams) in formic acid (5 grams), 1,4-dioxane (5 grams), water (5 grams), sodium formate (0.513 grams) and tetrabutylammonium iodide (0.687 grams) was heated to reflux under nitrogen and the reaction was monitored by thin layer chromatography ($CH_2Cl_2$ as eluent, silica gel). After 5 hours, the reaction was cooled, pH adjusted to 7 with aqueous sodium hydroxide solution, and reacidified with 0.2N HCl (pH 6). The mixture was extracted with ethyl acetate, and the ethyl acetate layer dried ($Na_2SO_4$), concentrated in vacuo to give a quantitative yield of the target diol. The material was shown by $^1H$ NMR to have the following structure (7).

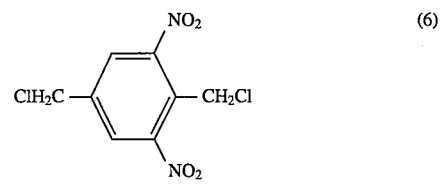

(6)

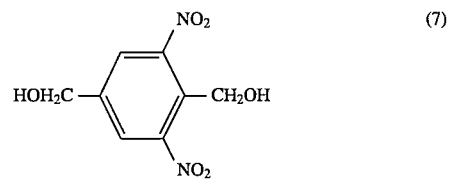

(7)

Monomers (6) or (7) may be reacted with a wide variety of comonomers to produce polymers having the photoactive dinitro groups of the present invention. A polyurethane can be prepared by the reaction of a diisocyanate with dinitro diol (7) as illustrated in Example 3 to generate compounds with structure (8):

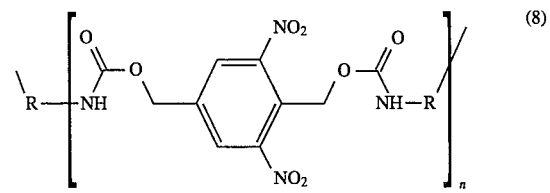

(8)

where n is 1 to infinity, and R is the residue of the diisocyanate.

Polyisocyanates, which are preferably diisocyanates, that may be used to react with the photoreactive monomers of the present invention include: aliphatic isocyanates such as alkylene isocyanates, e.g., trimethylene, tetramethylene, pentamethylene, hexamethylene, 1,2-propylene, 1,2-butylene, 2,3-butylene, 1,3-butylene, ethylidene and butylidene diisocyanates and the cycloalkylene isocyanates, e.g., 1,3-cyclopentane, 1,4-cyclohexane, 1,2-cyclohexane, and isophorone diisocyanates; aromatic isocyanates such as arylene isocyanates, e.g., m-phenylene, p-phenylene, 4,4'-diphenyl, 1,5-naphthalene and 1,4-naphthalene diisocyanates; alkarylene isocyanates, e.g., 4,4'-diphenyl methane, 2,4- or 2,6-tolylene, or mixtures thereof; 4,4'-toluidine, 1,4-xylylene, and recta- and paratetramethylxylene diisocyanates; and nuclear-substituted aromatic compounds, e.g., dianisidine diisocyanate, 4,4'-diphenylether diisocyanate and chlorodiphenylene diisocyanate. Triisocyanates such as triphenyl methane-4,4',4''-triisocyanate, 1,3,5-triisocyanato benzene and 2,4,6-triisocyanato toluene; the tetraisocyanates such as 4,4'-diphenyldimethyl methane-2,2',5,5'-tetraisocyanate; and polymerized polyisocyanates such as tolylene diisocyanate dimers and trimers and the like can also be used herein. In addition, the polyisocyanates may be prepolymers derived from polyols such as polyether polyols or polyester polyols, including polyols which are reacted with excess polyisocyanates, such as mentioned above, to form isocyanate-terminated prepolymers. Mono-isocyanates may also be reacted with the photoactive monomers of the present invention, including: phenyl, methyl, butyl, cyclohexane, and meta-isopropenyl-α,α-dimethylbenzyl isocyanates.

Aliphatic ethers can be prepared by condensation of dichloride (6) with propylene glycol to give an intermediate (9) as illustrated in Example 8, which can be condensed with diisocyanates to give polymer structure (10):

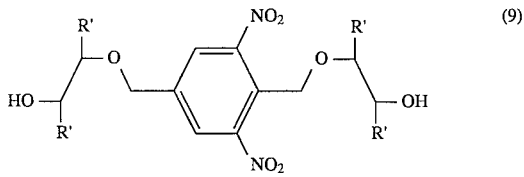

where R' is any combination of —CH₃ or —H.

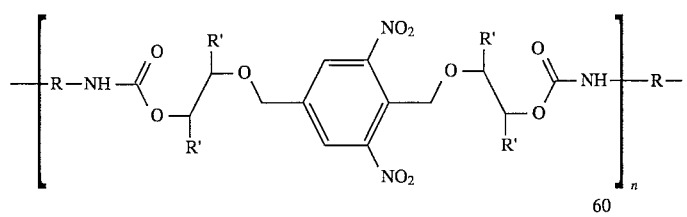

where n is 1 to infinity; and R is the residue of the isocyanate.

A dihydroxy diamine (11) may be derived by condensation of N-methyl-2-hydroxyethylamine with dichloride (6) as illustrated in Example 7, and the product may be condensed with a diisocyanate to prepare the polymer (12):

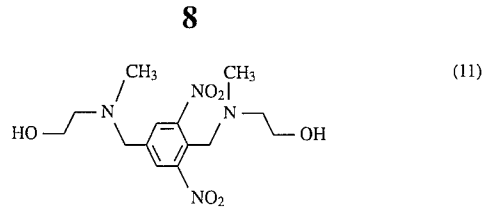

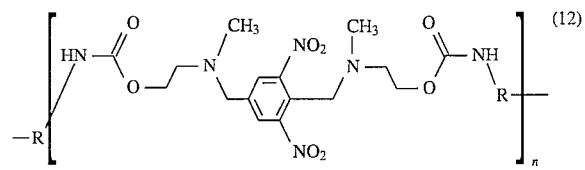

where n is 1 to infinity, and R is the residue of the isocyanate.

Diamine (11) may be converted to a quaternary amine (13) by condensation with an epoxide such as diglycidyl ether of bisphenol A (14):

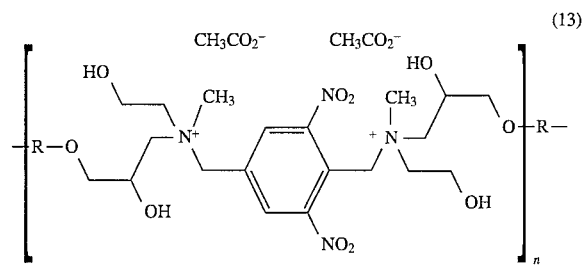

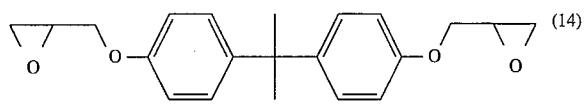

where n is 1 to infinity, and R is the residue of the epoxy compound.

Useful epoxy materials for reacting with the photoactive monomers of the present invention may be monomeric or polymeric compounds or a mixture of compounds having an average of one or more epoxy groups per molecule. Although monoepoxides can be utilized to make intermediates, polymeric products may use epoxy materials that contain more than one epoxy group per molecule. The epoxy materials can be essentially any of the well-known epoxides. Monoepoxies that may be used include ethylene oxide, propylene oxide, butylene oxide, phenyl glycidyl ether, butyl glycidyl ether, allyl glycidyl ether, and glycidyl methacrylate. A particularly useful class of polyepoxides are polyglycidyl ethers of polyphenols such as bisphenol A (structure 14), bisphenol F, 1,4-butanediol, or novolak resins. These can be produced, for example, by etherification of a polyphenol with epichlorohydrin in the presence of an alkali. The phenolic compound may be, for example, bis(4-hydroxyphenyl)2,2-propane, 4,4'-dihydroxy benzophenone, bis(4-hydroxyphenyl) 1,1-ethane, nonyl phenol, resorcinol, catechol, bis(4-hydroxyphenyl) 1,1-isobutane, bis(4-hydroxytertiarybutylphenyl)2,2-propane, bis(2-hydroxynaphthyl)methane, 1,5-dihydroxynaphthylene, or the like. In many instances, it is desirable to employ such polyepoxides having somewhat higher molecular weight and preferably containing aromatic groups. These polyepoxides can be made by reacting the diglycidyl ether set forth above with a polyphenol such as bisphenol A. Preferably, the polyglycidyl ether of a polyphenol contains free hydroxyl groups in addition to epoxide groups. While the polyglycidyl ethers of polyphenols may be employed per se, it is frequently desirable to react a portion of the reactive sites (hydroxyl or in some instances epoxy) with a modifying material to vary the film characteristics of the resin.

Another quite useful class of polyepoxides are produced similarly from novolac resins or similar polyphenol resins. Also suitable are the similar polyglycidyl ethers of polyhydric alcohols which may be derived from such polyhydric alcohols as ethylene glycol, diethylene glycol, triethylene glycol, 1,2-propylene glycol, 1,4-propylene glycol, 1,5-pentanediol, 1,2,6-hexanetriol, glycerol, bis(4-hydroxycyclohexyl)2,2-propane and the like. There can also be used polyglycidyl esters of polycarboxylic acids, which are produced by the reaction of epichlorohydrin or similar epoxy compounds with an aliphatic or aromatic polycarboxylic acid such as oxalic acid, succinic acid, glutaric acid, terephthalic acid, 2,6-naphthylene dicarboxylic acid, dimerized linolenic acid and the like. Examples are glycidyl adipate and glycidyl phthalate. Also useful are polyepoxides derived from the epoxidation of an olefinically unsaturated alicyclic compound. Included are diepoxides comprising in part one or more monoepoxides. These polyepoxides are non-phenolic and are obtained by the epoxidation of alicyclic olefins, for example, by oxygen and selected metal catalysts, by perbenzoic acids, by acetaldehyde monoperacetate, or by peracetic acid. Among such polyepoxides are the epoxy alicyclic ethers and esters which are well-known in the art. Other epoxy-containing compounds and resins include nitrogeneous diepoxides such as disclosed in U.S. Pat. Nos. 3,365,471; epoxy resins from 1,1-methylene bis(5-substituted hydantoin), 3,391,097; bisimide-containing diepoxides, 3,450,711, epoxylated aminoethyldiphenyl oxides, 3,312,644; heterocyclic N,N'-diglycidyl compounds, 3,503,979; amine epoxy phosphonates, British Patent 1,172,916; 1,3,5-triglycidyl isocyanurates, as well as other epoxy-containing materials known in the art.

Ester and polyesters such as (15) may be produced by condensation of any acid, diacid, or polyacid with dinitro diol (7). Providing the acid as a acid chloride may be preferred for the sake of greater reactivity, and therefore, structure (15) is the reaction product of dinitro diol with sebacoyl chloride as described with greater detail in Example 11:

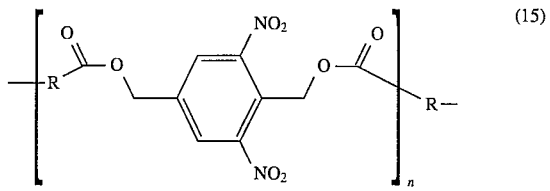

(15)

where n is 1 to infinity, and R is the residue of the sebacoyl chloride or any other acid residue.

Dichloride (6) may be condensed with p-t-butylphenol to prepare the diphenolic ether (16).

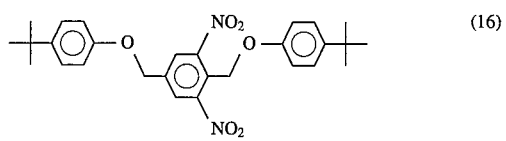

(16)

Another useful feature of dichloride (6) is its ability to be selectively condensed at one of the benzyl chlorides without effecting the other. For example, dichloride (6) has been selectively condensed with p-methoxyphenol to produce (17) and 2-mercaptoethanol to prepare (18).

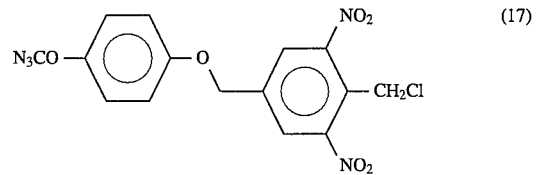

(17)

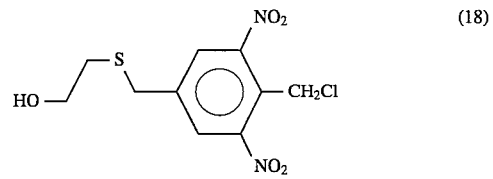

(18)

Disulfide monomers (19) may be synthesized from the dichloro monomer (6) and a mercaptan, and subsequently may be reacted with diisocyanates to yield thio containing polymers (20):

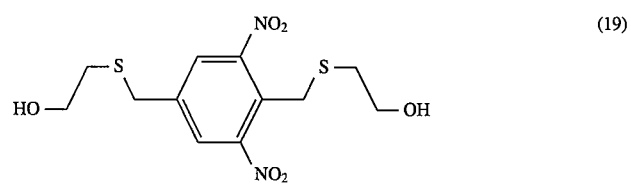

(19)

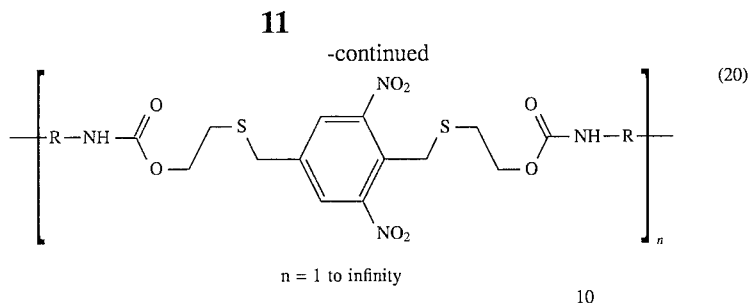

(20)

n = 1 to infinity where R is the residue of an isocyanate group.

EXAMPLE 3

PREPARATION OF PHOTOREACTIVE POLYURETHANE (A)

TMXDI® meta-tetramethylxylenediisocyanate from American Cyanamid ( 18.36 grams) was added dropwise to a 50° C. solution of 2,6-dinitrobenzene-1,4-dimethanol (7) (8.94 grams), N,N-dimethylbenzylamine (0.06 grams), and dibutyltin dilaurate (0.06 grams) in methyl isobutyl ketone (24.0 grams). The reaction was held for 1.5 hours at 60° C. to reach an isocyanate equivalent weight of 703. A solution of PPG 425 (polypropyleneglycol, 425 mol. wt., 15.80 grams) and methyl isobutyl ketone (4.00 grams) was then added dropwise over 1 hour, and the reaction held for an additional 6 hours. A trace of isocyanate remained by infrared spectroscopy so 2 drops of 2-butoxyethanol were added to quench the remaining isocyanate. The polyurethane was isolated at room temperature and had a solids content of 67.0%.

EXAMPLE 4

PREPARATION OF EPOXY-AMINE POLYMER (B)

Bisphenol A diglycidyl ether (446.69 grams) and bisphenol A diol (181.15 grams) were heated to 110° C. in methyl isobutyl ketone (40.00 grams). Ethyltriphenylphosphonium iodide (0.55 grams) was added and the mixture allowed to exotherm to 167° C. and then held at 160° C. for one hour. The reaction mixture was cooled to 110° C. and methyl isobutyl ketone (67 grams) was added to reduce viscosity. A mixture of dibutylamine (24.25 grams) and 2-(methylamino)ethanol (42.25 grams) was added and rinsed into the reactor with methyl isobutyl ketone (15.00 grams). After three hours the resin was cooled to room temperature and retained for later use. The resin was 92.2% solids.

EXAMPLE 5

CATIONIC DISPERSION OF PHOTOREACTIVE POLYURETHANE (A) AND

EPOXY-AMINE POLYMER (B)

Polyurethane A of Example 3 (52.8 grams), epoxy-amine B of Example 4 (46.9 grams), 2-butoxyethanol (4.00 gram), and lactic acid (85 %, 3.00 gram) were charged to a dispersion vessel. Deionized water (684 grams) was added slowly at a high stir rate to convert the resins to an aqueous dispersion. The residual methyl isobutyl ketone was stripped off by adding 100 grams of deionized water and stripping off 100 grams of volatiles under vacuum. The resulting dispersion had a particle size of 3970 angstroms and a solids content of 9.3%.

EXAMPLE 6

ELECTRODEPOSITION OF AN EPOXY-AMINE/URETHANE DISPERSION

An epoxy-amine/urethane dispersion, from Example 5 (9.3% solids), was filtered through a 400 mesh nylon filter (38.1 micron sieve size). The dispersion was heated to 100° F. (38° C.) with constant stirring. 2-Butoxyethanol (10.0 grams) and 2-hexyloxyethanol (6.0 grams) were added. The resin was reduced to 5 % solids with deionized water and placed into a cationic electrodeposition bath. A copper clad laminate substrate having ½ oz. copper per square foot (0.105 gram per square centimeter) was pre-cleaned with a detergent solution, followed by rinsing with deionized water and drying. The board was attached to a cathode, lowered into the electrodeposition bath (100° F., 38° C.), and current (80 volts) was applied for 90 seconds. A dehydration bake of 135° C. for 3 minutes yielded 0.26 rail (0.007 millimeter) film build. Voltages ranging from 40 to 110 volts generated film builds from 0.24 rail (0.006 millmeter) to 0.64 rail (0.016 millimeter). The resist was exposed to UV light through a Mylar photomask on an ORC Model HMW-532D UV exposure unit. The presence of the Mylar mask substantially filtered wavelengths below about 315 nanometers. The exposed board was then dipped into a developer consisting of 2.5% lactic acid (85 % in water) and 2.5% 2-butoxyethanol in deionized water heated to 88° F. (31° C.) with constant stirring. Development times to remove the photoexposed areas varied with a lower energy photoexposure (150 mJ/cm$^2$) requiring a development time of 2 minutes 20 seconds, and a higher energy (600 mJ/cm$^2$) requiring 1 minute 40 seconds development time.

EXAMPLE 7

SYNTHESIS OF 2,6-DINITRO-α, α'-DI(N-METHYL-N-2-HYDROXYETHYL)-P-XYLENE

This example illustrates an alternative route to a dinitro diol intermediate by way of amine condensation of the dichloro compound (6). A mixture of 2,6-dinitro-1,4-bis-(chloromethyl)benzene (6) (5.30 grams) and 1,4-dioxane (75 milliliters) was heated to 55° C. A solution of 2-(methylamino)ethanol (6.01 grams, 80 mmole) and dioxane (20 milliliters) was added over 1 hour. The reaction mixture was stirred at 55° C. for 6 hours until all starting material had been consumed. The reaction mixture was cooled to room temperature and filtered through silica gel to remove salts. The dioxane was removed under reduced pressure to give 5.47 grams (80%) of 2,6-dinitro-α,α'-bis(N-methyl-N-2-hydroxyethyl)-p-xylene, structure (11).

EXAMPLE 8

2,6-DINITRO-1,4-BIS(CHLOROMETHYL)BENZENE PROPYLENE GLYCOL

ADDUCT

This example illustrates an alternative route to producing dinitro diol intermediates by condensation of the dichloro compound (6) with glycol. A mixture of 2,6-dinitro-1,4-bis(chloromethyl)benzene (6) (50.0 grams) and basic aluminum oxide (45.0 grams) were suspended in propylene glycol (500 grams) and heated at 150° C. under a nitrogen atmosphere for 14 hours. During this time, low boiling distillate was removed via a Dean Stark apparatus. The reaction was followed to completion by thin layer chromatography. The contents were then cooled and vacuum filtered to remove the solid aluminum salts. Another portion of aluminum oxide (50 grams) was added to the supernatant liquid to remove any residual HCl, and was subsequently removed by filtration. At this time a portion of the excess propylene glycol was vacuum stripped from the product mixture at 90° C. and 1 mm Hg to yield 130 grams of a mixture comprised of approximately 50% 2,6-dinitro-1,4-bis (hydroxypropoxymethyl)benzene, structure (9), and 50% propylene glycol by weight.

EXAMPLE 9

PREPARATION OF PHOTOSENSITIVE POLYETHER/URETHANE FROM

ETHER INTERMEDIATE

This example illustrates the use of the intermediate of Example 8 to make a photosensitive polymer by reaction with diisocyanate. A mixture of tetramethylxylenediisocyanate (75.0 grams, 0.62 equivalents) and dibutyltin dilaurate (0.25 grams) were suspended in n-butyl acetate (75.0 grams) and heated to 70° C. under a nitrogen atmosphere. A solution of trimethylolpropane (2.0 grams) and the 2,6-dinitro-1,4-bis(hydroxypropoxymethyl)benzene propylene glycol mixture from Example 8 (50.0 grams) in n-butyl acetate (50.0 grams) was added over 1 hour via an addition funnel. The temperature was increased to 90° C. and the mixture was allowed to react until all of the isocyanate was consumed (approximately 8 hours) as determined by the disappearance of the N=C=O stretch in the infrared spectrum. The resulting resin was measured at 54.4% total nonvolatiles (110° C., 60 minutes).

EXAMPLE 10

PHOTOEXPOSURE AND DEVELOPMENT OF A MIXTURE OF A

POLYURETHANE-POLYETHER WITH AN ACID FUNCTIONAL RESIN

A copolymer of dimethyl maleate and undecylenic acid was synthesized as follows. Dimethyl maleate (216.0 grams) and undecylenic acid (184.0 grams) were charged to a reaction vessel equipped with a mechanical stirrer, thermocouple, condenser, and nitrogen inlet. The mixture was heated to 125° C. under a nitrogen atmosphere, and di-tertamyl peroxide (8.7 grams) was added via addition funnel over 30 minutes with no exotherm. The reaction was maintained at 125° C. for 11 hours and was then vacuum stripped at 210° C. to remove any unreacted monomers. The contents were cooled, and n-propanol (150 grams) was added to achieve a Gardner-Holdt viscosity of W-X. The resulting yellow resin was measured at 69.5% total nonvolatiles (110° C., 60 minutes), with an acid value of 95.3.

The polyurethane/polyether from Example 9 was blended with the copolymer of dimethyl maleate and undecylenic acid described above in a ratio of 95% urethane to 5.0% copolymer, and reduced to 30% solids in butyl acetate. The mixture was drawn down onto a copper clad laminate having ½ oz. per square foot (0.015 grams per square centimeter) employing a π20 wire (0.508 millimeter diameter wire) wound drawdown bar. The coated board was flashed for 10 minutes prior to being baked at 135° C. for 3 minutes. The film was exposed through a Mylar photomask to UV radiation for a total energy of 424 mJ/cm$^2$. The exposed substrate was dip developed for 1 minute 30 seconds in an aqueous base developer which was comprised of 1% sodium metasilicate pentahydrate and heated to 105° F. (40.5° C.) under constant stirring. The photoexposed film developed to the copper with minimal attack of the unexposed resist.

EXAMPLE 11

PREPARATION OF PHOTOREACTIVE POLYESTER

This example illustrates the use of dinitro diol to produce photoactive polyester polymer. Sebacoyl chloride (5.20 grams) was added dropwise to a solution of 2,6-dinitrobenzene-1,4-dimethanol, structure (7) (4.89 grams) and triethylamine (4.15 grams) in tetrahydrofuran (20.00 grams) at room temperature. The reaction mixture was heated to reflux for 30 minutes then cooled to room temperature and filtered to remove precipitated salts. The salts were rinsed with n-butyl acetate. The resin had a solids of 21.4 % and structure (15).

EXAMPLE 12

PHOTOEXPOSURE AND DEVELOPMENT OF THE PHOTOREACTIVE

POLYESTER

This example illustrates development of the photoreactive polyester of Example 11. The polyester from Example 11 was drawn down neat with a #20 wire (0.508 millimeter wire diameter) wound drawdown bar onto pre-cleaned, laminated substrate having ½ oz. copper per square foot (0.105 gram per square centimeter), allowed to flash for 10 minutes, and then baked for 3 minutes at 135° C. The postbaked film remained slightly tacky. The resist was exposed through a Mylar photomask with UV light of 424 mJ/cm$^2$ energy. An aqueous base developer (2% sodium recta-silicate pentahydrate in deionized water) at 105° F. (40.5° C.) dissolved the photoexposed resist to the copper in 16 minutes with the unexposed film remaining intact.

EXAMPLE 13

PHOTOEXPOSURE AND DEVELOPMENT OF THE PHOTOREACTIVE

POLYESTER WITH AN ACID FUNCTIONAL COPOLYMER

The copolymer derived from the polyester of Example 11 was blended with the copolymer derived from dimethyl maleate and undecylenic acid described in Example 10 in a ratio of 55 % copolymer to 45% polyester. A #20 wire (0.508 millimeter wire diameter) wound drawdown bar was used to coat the resin on a laminated substrate having ½ oz. copper per square foot (0.105 gram per square centimeter), then baked 3 minutes at 135° C. after a 10 minute flash time. The baked, unexposed film was tacky, but after exposure to UV radiation, exposed areas were dissolved readily using the same developer described in Example 12, and the unexposed areas remained unaffected.

EXAMPLE 14

SYNTHESIS OF 2,6-DINITRO-1,4-BIS(2-HYDROXYETHYLTHIOMETHYL)BENZENE

A 15% solution of sodium hydroxide (17 grams) in water was fed into mercaptoethanol (5 grams) over 10 minutes. This was stirred for 30 min to make solution I. Meanwhile, in a separate four necked flask, 8 grams of 2,6-dinitro-1, 4bis(chloromethyl)benzene (6) in 20 grams of methanol was stirred under $N_2$ at room temperature to make solution II. After 30 minutes, solution I was fed into solution II over 10 minutes at room temperature while maintaining temperature below 50° C. The reaction was held for 1 hour, analyzed by thin layer chromatography (2% $MeOH/CH_2Cl_2$, silica gel), and found to be complete. After addition of 20 grams of water to the reaction mixture, extraction with ethyl acetate and concentration in vacuo to gave 10 grams (95%) of crystalline 2,6-dinitro-1,4-bis(2-hydroxyethylthiomethyl)benzene (19). In a separate procedure the monosulfide intermediate (18) was the major product when triethylamine was used as base instead of sodium hydroxide. Both (18) and (19) were characterized by $^1H$ NMR.

EXAMPLE 15

PREPARATION OF ALIPHATIC POLYURETHANE BASED ON 2,6-DINITRO-1,4-BIS(2-HYDROXYETHYLTHIOMETHYL)BENZENE (19)

A mixture of 2,6-dinitro- 1,4-bis(2-hydroxyethylthiomethyl)benzene (19) (4 grams) from Example 14 and dibutyltin dilaurate (0.05 grams) in 10 grams of n-butyl acetate was heated to 50° C. Tetramethyl-m-xylene diisocyanate (5.62 grams) was added dropwise under $N_2$ atmosphere. The temperature of the reaction was adjusted to 60° C. and maintained for 1.5 hours. At this point the isocyanate equivalent weight was determined by titration and found to conform with the desired theoretical value (855). A solution of Arcol polypropylene glycol 425 (4.89 grams) in 5 grams of n-butyl acetate was then fed into the reaction over 1 hour and held until the isocyanate was completely consumed. The product was identified as structure (20).

EXAMPLE 16

PHOTOEXPOSURE AND DEVELOPMENT OF SULFIDE-CONTAINING POLYURETHANE

The polyurethane of Example 15 was reduced to 20 % solids with butyl acetate and blended with a copolymer (69.5% solids in n-propanol, acid value 95.3) of dimethyl maleate and undecylenic acid as described in Example 10. The blend ratio had a 55% by weight to 45% by weight ratio of copolymer to polyurethane. Final solids of the blend was 32.3%. The resin blend was drawn down with a #20 wire (0.508 millimeter wire diameter) wound drawdown bar onto a precleaned, laminated substrate having ½ oz. copper per square foot (0.105 gram per square centimeter). The substrates were allowed to flash 10 minutes, then baked at 135° C. for 3 minutes. The resist coated laminate was exposed to UV light of 424 $mJ/cm^2$ energy. The exposed panel was dip developed in 2 % aqueous sodium metasilicate pentahydrate at 105° F. (40.5° C.) with constant agitation for 2 minutes, then rinsed with water. The exposed portions of the film were removed with the rinse and the unexposed portion of the film remained intact. Another exposed panel was dipped developed for 1 minute, rinsed, and then placed in a solution of ferric chloride at room temperature for 15 minutes. The copper in the developed areas etched nicely and the unexposed film remained intact, protecting the copper underneath.

The invention has been described with reference to particular embodiments for the sake of providing the best mode of carrying out the invention, but it should be understood that other alternatives and variations known to those of skill in the art may be resorted to without departing from the scope of the invention as defined by the claims which follow.

We claim:

1. A photoactive compound including the structure:

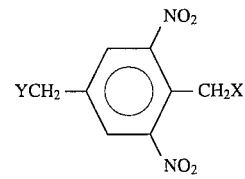

where X and Y may be the same or different member selected from the group consisting of: halogen, —OR, —O—$SO_2$R, —SR, —NRR', —OC=ONHR, —OC=OOR and —OC=OR; and where R and R' may be the same or different member selected from the group consisting of: hydrogen and substituted or unsubstituted alkyl, aryl, or aralkyl substitutents.

2. The compound of claim 1 wherein X and Y are selected from the group consisting of halogen and hydroxyl groups.

3. The compound of claim 2 wherein X and Y are the same.

4. The compound of claim 2 wherein X and Y are different from each other.

5. The compound of claim 2 wherein X and Y are halogen.

6. The compound of claim 5 wherein X and Y are chloride.

7. The compound of claim 1 wherein X and Y are hydroxyl groups.

8. The compound of claim 1 wherein, when R or R', or both are a substituted or unsubstituted alkyl, aryl, or aralkyl substitutent, the substituted includes chloride or a hydroxyl group.

9. The compound of claim 1 wherein at least one of X and Y is a urethane, carbonate, carboxylic acid ester, ether or sulfide.

10. A photoactive compound including the structure:

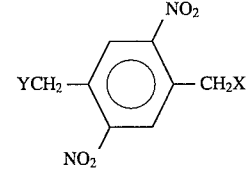

where X and Y are different from each other and selected from the group consisting of: halogen, —OR, —O—$SO_2$R, —SR, —NRR', —OC=ONHR, —OC=OOR and —OC=OR; and where R and R' may be the same or different member selected from the group consisting of: hydrogen and substituted or unsubstituted alkyl, aryl, or aralkyl substitutents.

11. The compound of claim 10 wherein X and Y are selected from the group consisting of hydrogen and hydroxyl groups.

12. The compound of claim 11 wherein X and Y are halogen.

13. A photoactive compound including the structure:

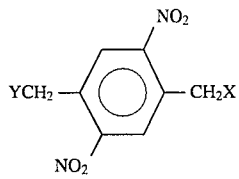

where X and Y are chloride.

14. The compound of claim 10 wherein, when R or R', or both are a substituted or unsubstituted alkyl, aryl, or aralkyl substituent, the substituted includes chloride or a hydroxyl group.

15. The compound of claim 10 wherein at least one of X and Y is a urethane, carbonate, carboxylic acid ester, ether or sulfide.

16. A photoactive compound including the structure:

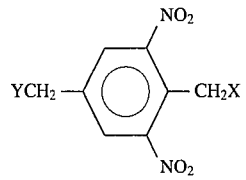

or

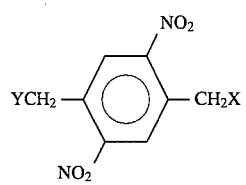

where X and Y may be the same or different member, and wherein at least one of X or Y is a polymeric urethane, carbonate, carboxylic acid ester, ether or sulfide.

17. The compound of claim 16 wherein X and Y are the same.

18. The compound of claim 16 wherein X and Y are different from each other.

* * * * *

UNITED STATES PATENT AND TRADEMARK OFFICE
CERTIFICATE OF CORRECTION

PATENT NO. : 5,600,035

DATED : February 4, 1997

INVENTOR(S) : Charles F. Kahle, II, et al.

It is certified that error appears in the above-identified patent and that said Letters Patent is hereby corrected as shown below:

Claim 11, line 2:   Delete [hydrogen] and insert --halogen--

Signed and Sealed this

Seventh Day of July, 1998

Attest:

BRUCE LEHMAN

Attesting Officer

Commissioner of Patents and Trademarks